US006939979B2

(12) United States Patent
Rizkalla et al.

(10) Patent No.: US 6,939,979 B2
(45) Date of Patent: Sep. 6, 2005

(54) OXIDATION PROCESS AND CATALYST

(75) Inventors: Nabil Rizkalla, Riverdale, NJ (US); Vijay S. Bhise, North Caldwell, NJ (US)

(73) Assignee: Scientific Design Co., Inc., Little Ferry, NJ (US)

( * ) Notice: Subject to any disclaimer, the term of this patent is extended or adjusted under 35 U.S.C. 154(b) by 72 days.

(21) Appl. No.: 10/714,378

(22) Filed: Nov. 10, 2003

(65) Prior Publication Data

US 2005/0101790 A1 May 12, 2005

(51) Int. Cl.$^7$ ............................................. C07D 301/10
(52) U.S. Cl. ...................................................... 549/533
(58) Field of Search ........................................ 549/533

(56) References Cited

U.S. PATENT DOCUMENTS 5,739,075 A * 4/1998 Matusz ........................ 502/302

* cited by examiner

Primary Examiner—Taofiq Solola
(74) Attorney, Agent, or Firm—Roberts & Roberts, LLP

(57) ABSTRACT

Ethylene is oxidized by contact at oxidizing conditions with an admixture of a solid particulate catalyst and a solid particulate alkali metal treated inert.

3 Claims, No Drawings

OXIDATION PROCESS AND CATALYST

BACKGROUND OF THE INVENTION

1. Field of the Invention

The present invention relates to an oxidation process such as the oxidation of ethylene to ethylene oxide wherein the oxidation is carried out using a fixed bed solid catalyst which comprises a mixture of a solid active oxidation catalyst such as a supported silver catalyst together with an inert diluent solid which has been treated with a base.

2. Description of the Prior Art

In the field of ethylene oxidation to ethylene oxide, it is taught to use beds of graded catalyst activity (British Patent 721,412) and to provide systems where reactor effluent is rapidly cooled by contact with inert solids; see U.S. Pat. Nos. 4,061,659, 4,376,209, 5,292,904, and 4,642,360.

A problem which has existed in such systems where the oxidation catalyst has been diluted with inert material has been the tendency for the inert diluent solid to actually promote degradation of the desired product. In other words, the inert diluent is generally not completely inert but rather has active surface sites which promote product loss.

BRIEF DESCRIPTION OF THE INVENTION

In accordance with the present invention it has been found that the unwanted loss of ethylene oxide product caused by catalyst dilution with inerts can be essentially obviated by subjecting the inert diluent to treatment with a base prior to admixture with the active catalyst.

DETAILED DESCRIPTION

In the process of charging a commercial reactor with a supported catalyst e.g. a Ag/alumina catalyst for ethylene oxidation to ethylene oxide, it may be important to add an inert material within the catalyst bed for stratification or dilution. Alternatively, an inert material may be added at the bed's outlet. In either case it is highly desirable that the inert material is of the same size and configuration as the catalyst particles, or pellets. The most suitable material that can be used as an inert is the same carrier that is used in the catalyst's preparation. We have discovered that treating the carrier with any of the alkali metals renders it inert and suitable for using in catalyst bed dilution or stratification while substantially avoiding product loss.

In the case of conventional ethylene oxidation, the carrier of choice for the silver catalyst is alumina. However, as normally provided, the alumina carrier has an active surface that can cause the degradation of the product, ethylene oxide. We have discovered that depositing a small amount of any of the salts of alkali metals on the carrier's surface neutralizes this activity and renders the carrier's surface inert so as to avoid degradation of the product.

In the prior art, salts of the "higher alkali metals" were used in catalyst preparation to improve the catalytic performance. Cesium is the most common additive, although additive mixtures of Cs and another alkali metal are also claimed to improve the catalytic performance. The "lower alkali metals", Li and Na, were reported to give an insignificant improvement. In these catalyst preparations, however, the alkali metal treated carrier also contains silver and other promoters.

Most commercially available catalyst carriers contain one or more of the alkali metal salts, especially sodium. The portion of this native alkali metal that is present on the surface plays a role in neutralizing some of the destructive sites on the carrier's surface. We have discovered that the removal of the surface native alkali metal salts will increase the surface activity, and also the destructive propensity of the carrier. The amount of these surface native alkali metals normally found in the carrier, however, is not sufficient to neutralize all the destructive sites. Therefore, depositing an additional amount of the alkali metal is essential to obtain a totally inactive surface in accordance with the invention.

It is difficult to estimate the minimum amounts of the alkali metal salts that are required to neutralize all the destructive sites on the carrier's surface. The amount of active sites is a function of many factors, e.g. the surface area of the carrier, the different additives used in its formulation, the carrier's calcinations process, as well as the chemistry of its surface. There is, however, no harm in adding a large amount of the alkali metal salts, larger than that which is needed to neutralize all the active cites. In general the amount of alkali metal salt on the surface should be more than 5 milligram atom/kg carrier up to about 2 wt % of the inert support. Alkali metal salts used in the invention include salts of sodium, potassium, rubidium, and cesium.

The concentration of the different alkali metals on the carrier's surface is generally determined via the acid-leachables test. In the acid-leachables test, the carrier sample is digested in a nitric acid solution. The alkali metals' concentration in the resulting solution is determined by atomic absorption spectro-photometry, Varian AA-110, in an air/acetylene flame. Alternatively, quantification is performed by aspirating the solutions into an inductively coupled plasma spectrophotometer, Spectro-analytical EOP ICP.

In carrying out the present invention, the inert particular solid, which has been base treated, is admixed with conventional oxidation catalyst to the extent necessary to achieve the desired dilution.

In the case of ethylene oxide production, the treated inert is admixed with a conventional supported silver catalyst such as is described in U.S. Pat. Nos. 5,504,052, 5,646,087, 5,7736,483, 5,703,001, 4,356,312, 4,761,394, and the like, the disclosures of which are incorporated herein by reference.

In the base treatment, the inert support is appropriately immersed in an aqueous solution of an alkali metal compound such as the hydroxide, carbonate, acetate, and the like for a time sufficient to deposit the basic material on the support surface, e.g. one (1) minute to ten (10) hours or more. The support is removed from the basic solution and dried, and is then suitable for blending with the solid oxidation catalyst.

Generally speaking, the base treated inert is blended in amounts ranging from about 5 to 80 wt % of the combined weight of the inert and catalyst although, as above indicated the base treated inert can comprise 100% of the solids in a preheat section of the reactor tube.

EXAMPLES

Example 1

Comparative Example

An ethylene oxide catalyst was prepared by impregnating an alpha-alumina carrier with an aqueous solution of Ag oxalate/ethylene diamine complex the carrier was cylinducial with an outer diameter of 8 mm, a height of 8 mm, and a bore having a diameter of 5 mm. The solution also contained a salt of Cs, promoter. The catalyst was calcined at temperature sufficient to decompose the silver complex to its metallic form. The catalyst obtained contained 12% Ag and 500 ppm Cs. This catalyst was used in all the following examples.

The catalyst was tested by charging 9 g to a stainless steel reactor tube which was then heated by a molten salt bath. A gas mixture comprising 15% ethylene, 7% oxygen, and 78% inerts, mainly nitrogen and carbon dioxide, was passed through the catalyst at 300 psig. The temperature of the reaction was adjusted in order to obtain ethylene oxide productivity of 160 Kg per hour per $m^3$ of catalyst. After one week of reaction time the performance of the catalyst was stable and the calculated selectivity, to ethylene oxide, was 83.3%.

Example 2

Comparative Example

The purpose of this example is to determine the destructive effect of the activity of the carrier's surface, on ethylene oxide production.

A similar charge of 9 g catalyst was charged to the stainless steel reactor tube. In this example, 2 g of the same alumina carrier that was used in the catalyst preparation was also added in admixture with the catalyst. The carrier was placed in the upper third of the reactor tube. After one week of reaction time the performance of the catalyst was stable and the calculated selectivity to ethylene oxide was 81.9%.

Example 3

100 g of the same carrier that was used in the catalyst preparation and which had a surface Na concentration of 90 ppm was washed with 500 ml of 0.3 N solution of ammonium hydroxide in water. The solution was drained and the washing process was repeated four more times. The carrier was than washed twice with de-ionized water and dried at 150° C. Analysis of the drained solutions showed that the total amount of sodium that was removed from the surface of the carrier was 55 ppm.

9 g catalyst was charged in the stainless steel reactor tube. In this example also, 2 g of the washed carrier was added. The carrier was placed in the upper third of the bed.

After one week of reaction time the performance of the catalyst was stable and the calculated selectivity, to ethylene oxide, was 80.3%. This demonstrates that removal of the native surface sodium, via washing with the ammonium hydroxide solution, has increased the destructive propensity of the carrier.

Example 4

100 g of the carrier that was used in the catalyst preparation was impregnated with 300 ml of aqueous 0.05 N cesium hydroxide solution. The carrier was dried and analyzed for its Cs content, using the acid leachable test. The carrier contained 300 ppm Cs.

9 g catalyst was charged to the stainless steel reactor tube. In this example also, 2 g of the Cs-treated carrier was added. The carrier was placed in the upper third of the bed as in Example 3. After one week of reaction time the performance of the catalyst was stable and the calculated selectivity to, ethylene oxide, was 83.3%. This demonstrates that the Cs treatment has neutralized the destructive active sites on the carrier's surface and substantially reduced ethylene oxide.

Example 5

A sample of the carrier was treated with 300 ml of 0.05 N aqueous solution of cesium carbonate. After the treatment, analysis showed that the carrier contained 570 ppm cesium. 2 g sample of this treated carrier was added to the catalyst bed, as above. After one week of reaction time, the performance of the catalyst was stable and the calculated selectivity to, ethylene oxide, was 83.2%. This demonstrates that the Cs treatment has neutralized the destructive active sites on the carrier's surface.

Examples 6–8

Samples of the carrier were treated with aqueous solutions of the hydroxides of Li, Na, and K as illustrated in example 3. The treated carriers were then analyzed for their leachable contents of the respective alkali metal. 2 g sample of each of the treated carrier was added to a separate reactor tube containing 9 g of the silver catalyst, as illustrated in FIG. 1.

After one week of reaction time the performance of the three catalysts was stable and the selectivity, to ethylene oxide, was determined, table 1:

TABLE 1

| Example | Carrier | Selectivity of the catalyst % |
|---|---|---|
| 6 | α-alumina carrier treated with NaOH (150 ppm Na) | 83.4 |
| 7 | α-alumina carrier treated with KOH (260 ppm K) | 83.2 |
| 8 | α-alumina carrier treated with LiOH (50 ppm Li) | 83.2 |

This demonstrates that in each of the three cases the alkali metal treatment has neutralized the destructive active sites on the carrier's surface.

We claim:

1. In a process for the molecular oxidation of ethylene with a solid particulate oxidation catalyst to form ethylene oxide, the improvement which comprises oxidizing the ethylene by contact with an admixture of a solid particulate oxidation catalyst and a solid particulate inert which has been treated with an alkali metal salt.

2. The process of claim 1 wherein the particulate inert is alumina.

3. The process of claim 1 wherein the oxidation catalyst comprises silver supported on alumina.

* * * * *